(12) United States Patent
Smith (10) Patent No.: US 9,180,037 B1
(45) Date of Patent: Nov. 10, 2015

(54) LEG BRACE

(76) Inventor: Joel N. Smith, Edmonds, WA (US)

( * ) Notice: Subject to any disclaimer, the term of this patent is extended or adjusted under 35 U.S.C. 154(b) by 0 days.

(21) Appl. No.: 13/098,309

(22) Filed: Apr. 29, 2011

Related U.S. Application Data (63) Continuation-in-part of application No. 12/844,118, filed on Jul. 27, 2010, now abandoned.

(60) Provisional application No. 61/229,180, filed on Jul. 28, 2009.

(51) Int. Cl.
*A61F 5/00* (2006.01)
*A61F 5/01* (2006.01)

(52) U.S. Cl.
CPC ............................ *A61F 5/0111* (2013.01)

(58) Field of Classification Search
USPC ............... 602/5, 23–29, 62, 65; 128/888, 128/845–846, 882, 891–892; 135/65, 69, 135/67, 75
See application file for complete search history.

(56) References Cited

U.S. PATENT DOCUMENTS

| | | | | |
|---|---|---|---|---|
| 2,558,986 | A * | 7/1951 | Seelert | 602/16 |
| 3,316,900 | A * | 5/1967 | Young | 602/16 |
| 3,906,942 | A * | 9/1975 | Lumb et al. | 602/40 |
| 6,206,018 | B1 * | 3/2001 | Daniels, Jr. | 135/69 |
| 2002/0077576 | A1 | 6/2002 | Saraceni | |
| 2003/0213510 | A1 * | 11/2003 | MacCready et al. | 135/65 |
| 2008/0208094 | A1 * | 8/2008 | Gaylord | 602/23 |

* cited by examiner

*Primary Examiner* — Ophelia A Hawthorne
(74) *Attorney, Agent, or Firm* — Christensen O'Connor Johnson Kindness PLLC (57) ABSTRACT

A leg brace includes a frame and a stirrup coupled to a lower end of the frame for engaging a ground surface during use. The leg brace further includes a first attachment assembly coupled to an upper end of the frame that is configured to removably secure the frame to a first portion of a user's leg and a second attachment assembly coupled to a lower end of the frame that is configured to removably secure the frame to a second portion of a user's leg.

16 Claims, 7 Drawing Sheets

LEG BRACE

CROSS-REFERENCES TO RELATED APPLICATIONS

This application is a continuation-in-part of U.S. patent application Ser. No. 12/844,118, filed Jul. 27, 2010, which claims the benefit of U.S. Provisional Application No. 61/229,180, filed Jul. 28, 2009, the disclosures of which are hereby expressly incorporated by reference.

BACKGROUND

When a person injures his or her foot, ankle, knee, or another portion of the leg, he or she is often required to refrain from applying any pressure to the injured area for a predetermined period of time prescribed for recovery. This typically requires that the person refrain from walking. To remain mobile, the injured person may use a mobility device, such as a wheelchair, crutches, a leg scooter, etc., as an aid when moving around. Although a wheelchair, crutches, or a leg scooter is effective in allowing the person to move independently without applying pressure to the injured area, none of the above-mentioned mobility devices allows the injured person to move around freely without restrictions or limitations.

For instance, a wheelchair is limited to buildings, vehicles, public spaces, or other areas that have wheelchair-accessible entrances, pathways, lifts, etc. Many buildings, vehicles, and public spaces are not wheelchair accessible; and as a result, the person must refrain from going certain places or engaging in certain activities. Moreover, using a wheelchair requires the use of at least one hand to either operate an electronic control panel or to drive the wheels of the chair. Thus, a person's hands are restricted when moving around in the wheelchair.

Crutches require the use of the person's arms to balance and move the crutches when moving the body on the non-injured foot and leg to the desired location. As such, the person cannot do many simple things while using crutches, for instance, carrying a cup of coffee, opening a door, etc. Moreover, to move on crutches, the person essentially plants the bottom of the crutches forward of his body and then "swings" his body and the weight-bearing leg forward to a new position. During this swinging movement, the person must balance on the crutches. Because this requires significant arm strength, the person normally ends up bracing the upper end of the crutch within his armpit or against the inner portion of his arm to relieve some of the load on his arms. As a result, not only do the person's arms tire, but he typically acquires bruises or sore spots beneath his arms. In addition, because of the difficulty balancing on crutches, it is often difficult and dangerous for the injured person to go up and down stairs, further restricting the mobility of the injured person.

The leg scooter has been recently developed to give an injured person the increased mobility of crutches without having to strain the arms during use. The scooter typically includes a platform on which the lower half of the leg may rest, wherein the platform is moveably suspended above the ground through a wheel system. A handlebar is coupled to the scooter, the handlebar being grippable while moving to improve balance. An example of a well-known leg scooter available to the public is the Roller Aid™ leg scooter available from Enhanced Mobility System, Inc., of Spokane, Wash. Such a leg scooter is more versatile than a wheelchair in that it can fit in smaller spaces; however, the person is still restricted to areas having ramps, platforms, etc., to move from a first level to a second level. Moreover, the person's arms are not completely free while moving since it is normally necessary to hold onto the handlebars while moving. Further, the leg scooter may only be used for injuries below the knee since the knee must rest on the leg scooter during use.

Thus, there is a need for a mobility device for use by a person having a leg injury, and particularly an injury of the foot, ankle, knee, or any other area below the knee, that isolates the injured area without substantially limiting the person's mobility and without restricting use of his or her arms while moving.

The need for such a mobility device may also arise for a person who has lost a portion of his or her leg. Modem prosthetic limbs can go a long way in helping amputees to regain essential capabilities. Moreover, prosthetic limbs can be constructed such that the prosthetic limb gives the amputee the sensation or feeling that it is a part of the leg.

However, because each patient and his or her amputation is unique, each prosthetic limb must be custom fitted and then built for that person. This process is not only costly the first time, but the prosthetic limb must also be replaced or refitted as the person's body changes due to atrophy of the muscles, growth, etc.

Thus, there is also a need for a low-cost mobility device that may be adapted for use by persons with varying leg amputations and that may be adjusted to accommodate changes in body size.

SUMMARY

A leg brace includes a frame, a stirrup coupled to a lower end of the frame for engaging a ground surface during use, and an attachment assembly coupled to an upper end of the frame, the attachment assembly configured to removably secure the frame to a user's leg.

In another embodiment, a leg brace includes a frame and a stirrup coupled to a lower end of the frame for engaging a ground surface during use. The leg brace further includes a first attachment assembly coupled to an upper end of the frame that is configured to removably secure the frame to a first portion of a user's leg and a second attachment assembly coupled to a lower end of the frame that is configured to removably secure the frame to a second portion of a user's leg.

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

DESCRIPTION OF THE DRAWINGS

The foregoing aspects and many of the attendant advantages of the present disclosure will become more readily appreciated by reference to the following detailed description, when taken in conjunction with the accompanying drawings, wherein.

DETAILED DESCRIPTION

Figure 1:
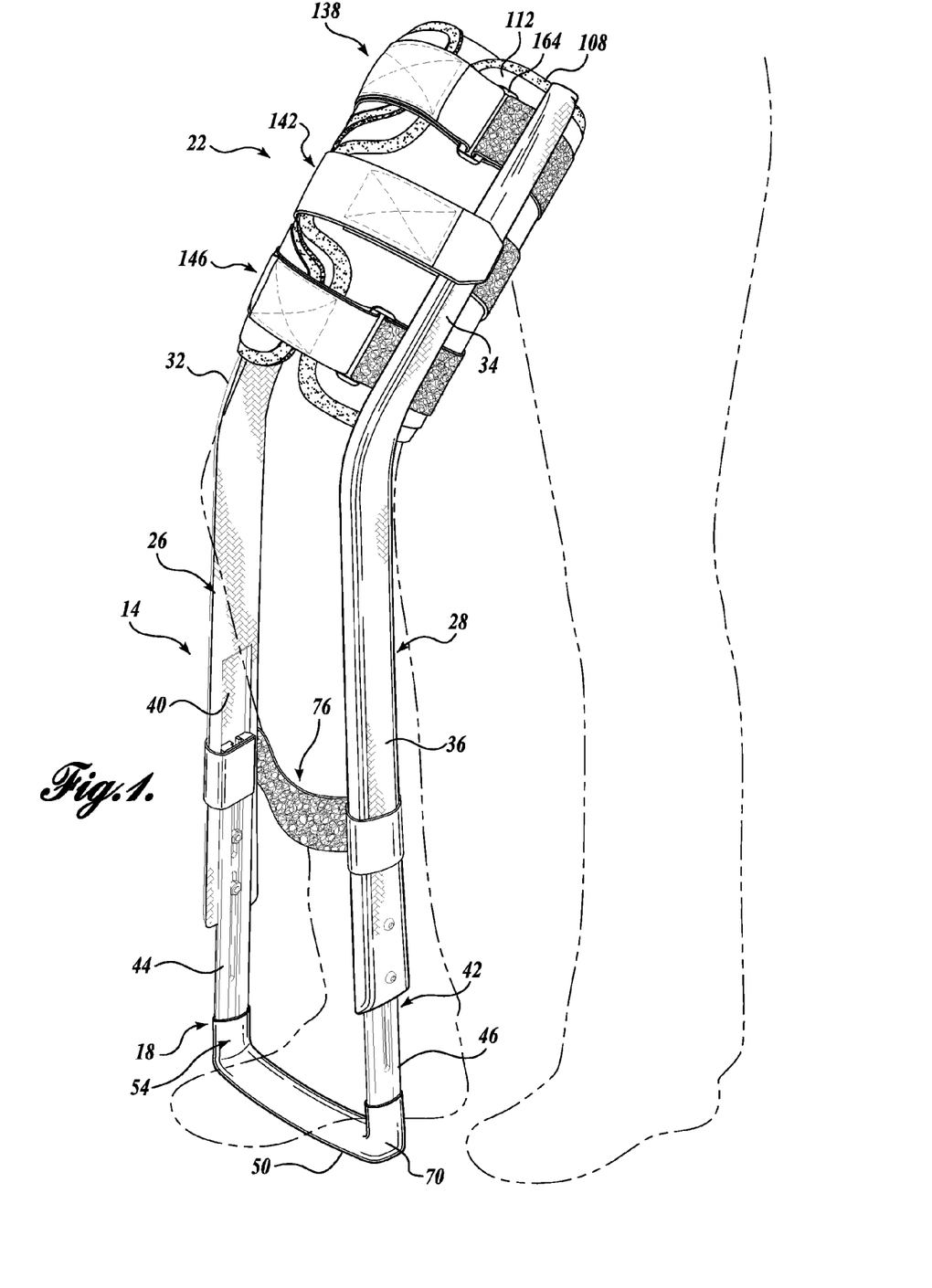
FIG. 1 is an isometric view of a leg brace formed in accordance with a preferred embodiment of the present disclosure, wherein the leg brace is shown in use on a person's leg.

Referring to FIG. 1, a leg brace 10 formed in accordance with a preferred embodiment of the present disclosure is depicted. The leg brace 10 includes a frame 14, a stirrup 18 coupled to the lower end of the frame 14 for engaging the ground during use, and an attachment assembly 22 coupled to the upper end of the frame 14 for removably securing the leg brace 10 to a portion of a person's leg. The leg brace 10 is secured to the leg of a user to essentially act as a prosthetic for the injured or amputated leg to allow the person to walk in a substantially normal fashion. Moreover, the leg brace 10 allows a person to be completely mobile without applying any pressure to the injured portion of the leg (in the case of an injury) and without substantially restricting the person's ability to move and use his or her arms while moving. The leg brace 10 will be hereinafter described with reference to an injured knee; however it should be appreciated that the leg brace 10 may also be used with any injury below the knee or with an amputation of a portion of the leg. Thus, the following description should not be seen as limiting the scope of the present disclosure.

Figure 2:
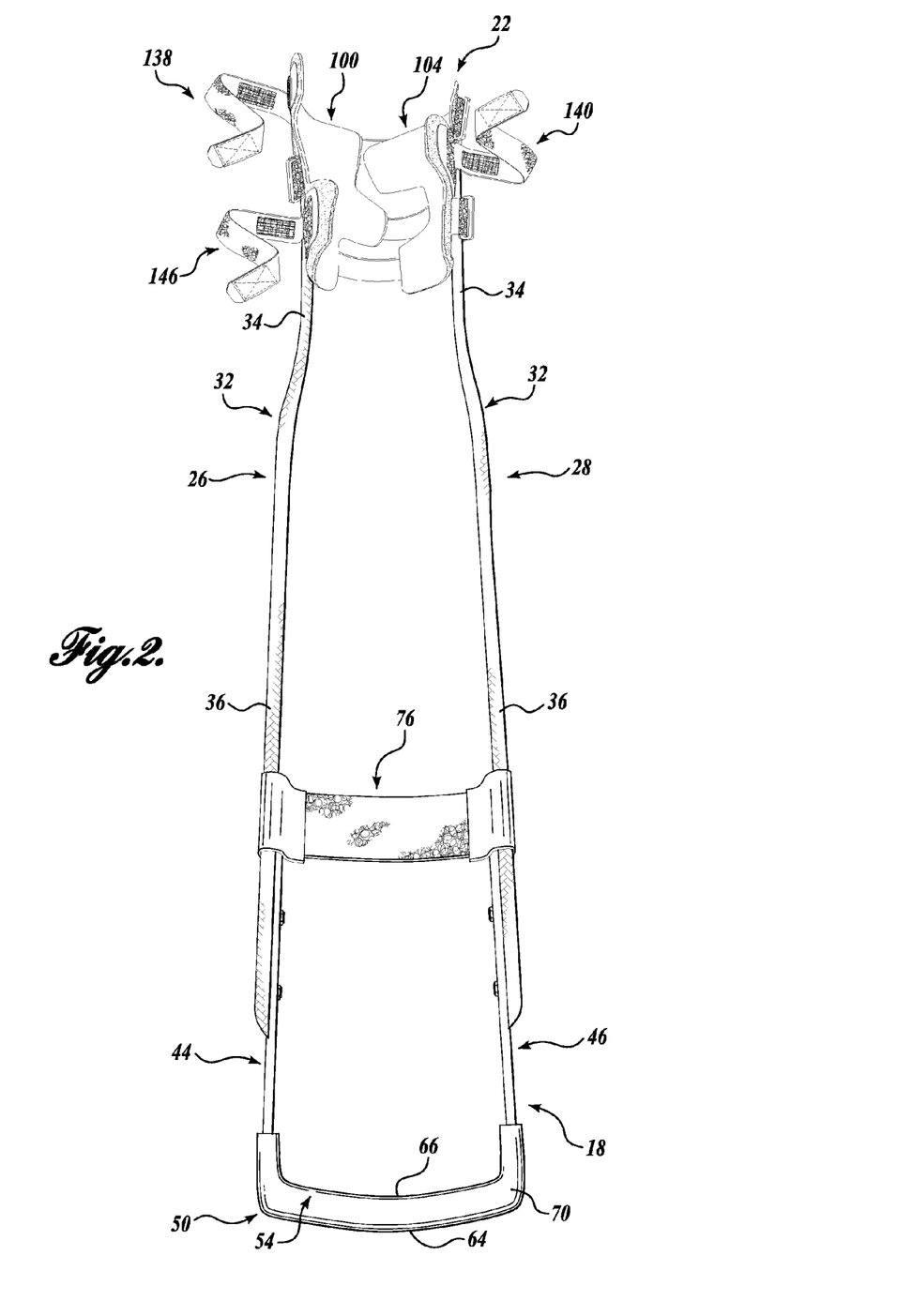
FIG. 2 is a front view of the leg brace of FIG. 1.

Referring to FIGS. 1 and 2, a preferred embodiment of the frame 14, which is suitable for transferring loads from the ground to an upper portion of the person's leg, will now be described in detail. The frame 14 includes first and second frame members 26 and 28 that are substantially identical in size and shape. The first and second frame members 26 and 28 are of a length sufficient to extend from just below the hip of a person to at least below the knee of the person when the members 26 and 28 are positioned along the length of the leg. It should be appreciated that the leg brace 10 may be available to consumers and patients in several different sizes with the length of the frame members 26 and 28 being made longer or shorter for the different sizes.

The first and second frame members 26 and 28 may each include a slight bend to define an elbow 32 between an upper frame portion 34 and a lower frame portion 36. The upper frame portion 34 extends rearwardly from a vertical axis defined by the lower frame portion 36 to substantially mirror the bend in a person's leg when injured, or when recovering from surgery, etc. For instance, it is common when recovering from an injury or surgery that a person's knee be somewhat swollen, which makes it difficult to fully straighten the leg. As such, the shape of the first and second frame members 26 and 28 accommodates any bend in the knee caused by swelling, bandages, etc., when secured to the leg by the attachment assembly 22.

Figure 5:
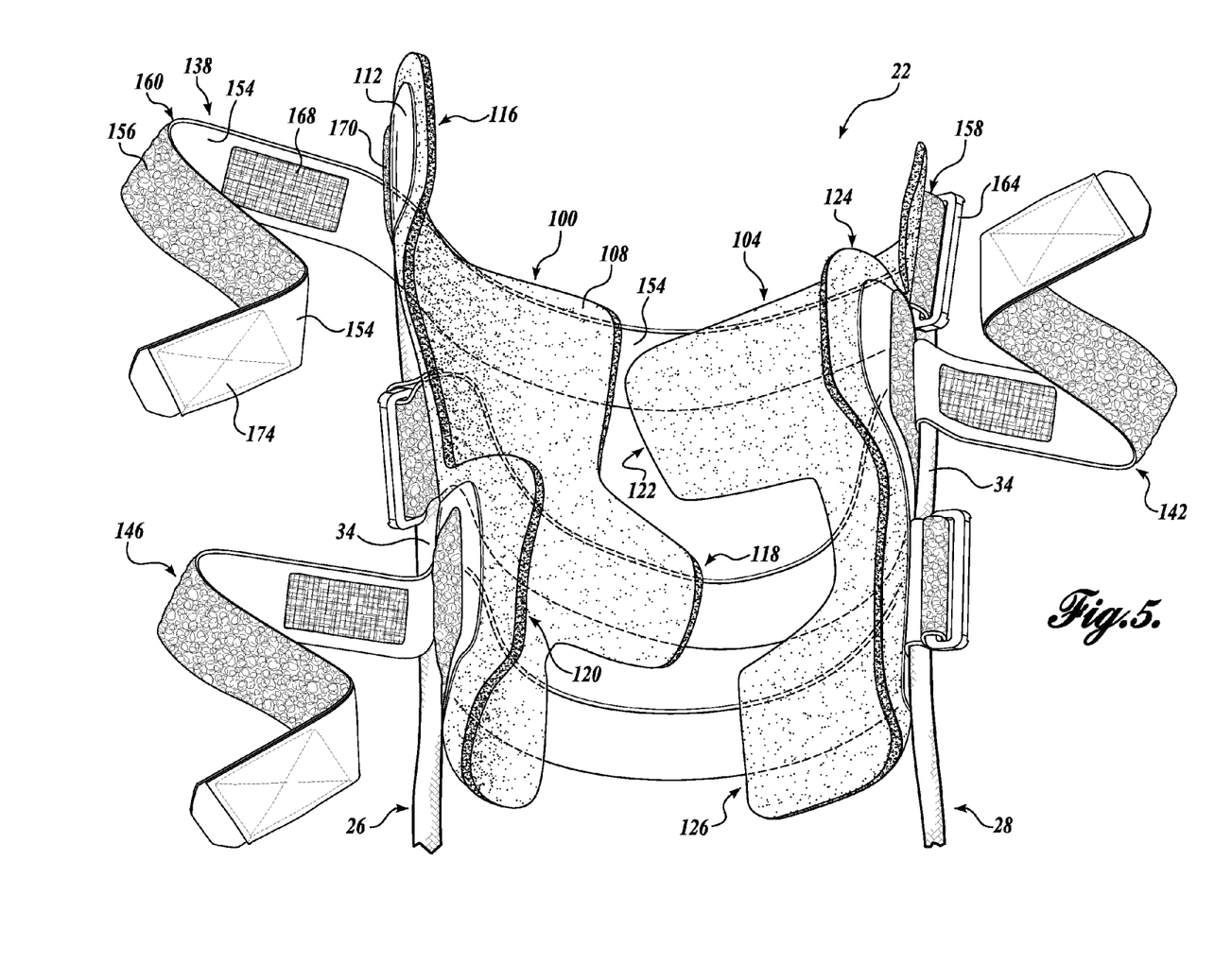
FIG. 5 is a front view of an upper portion of the leg brace of FIG. 1.
Figure 6:
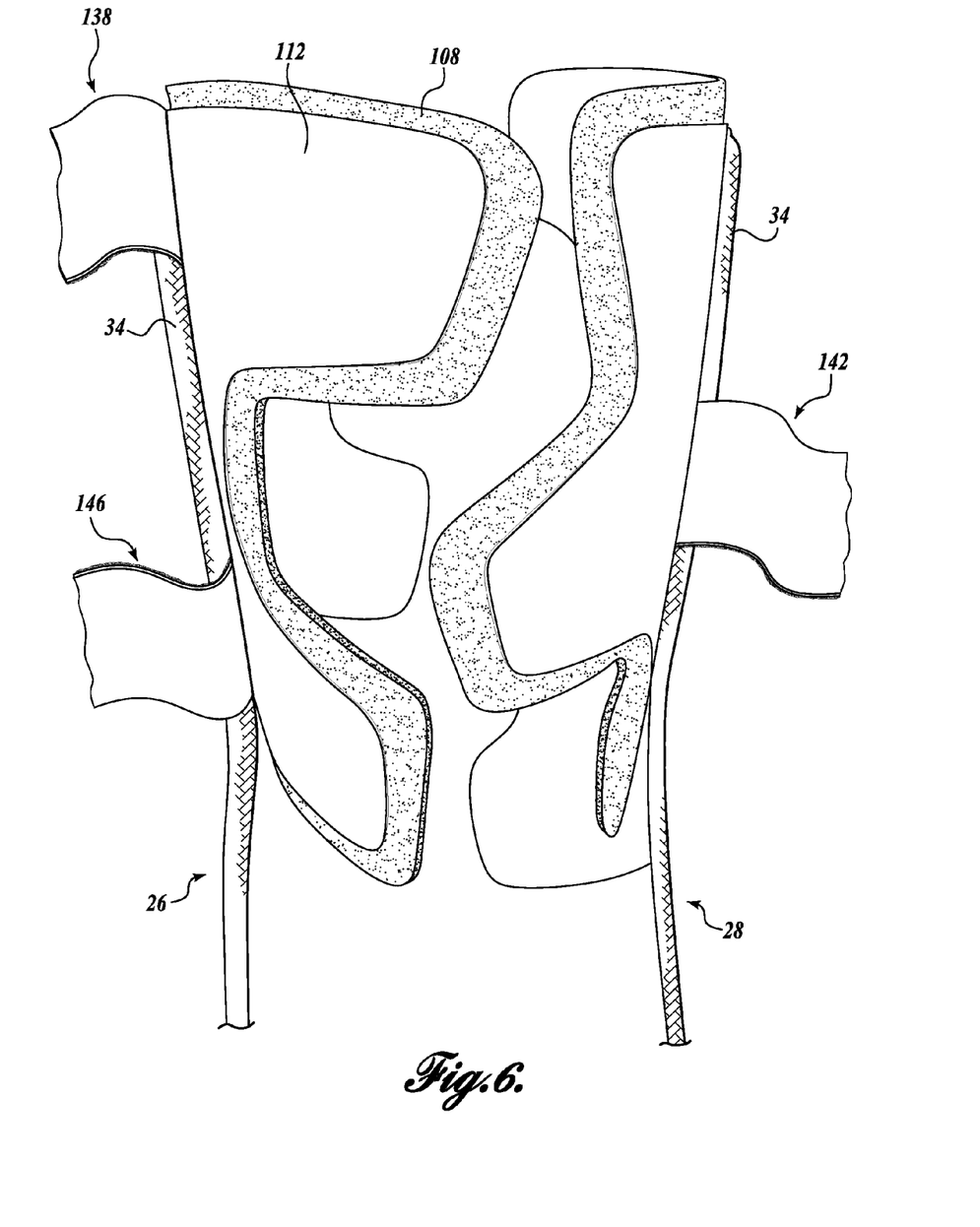
FIG. 6 is a rear view of an upper portion of the leg brace of FIG. 1.

The upper frame portion 34 of each of the first and second frame members 26 and 28 extend at least somewhat outwardly from the elbow 32 to accommodate the frusto-conical shape of a person's thigh when received within the attachment assembly 22 (see FIGS. 2, 5, and 6). Moreover, it is also preferred that the lower frame portions 36 of the first and second frame members 26 and 28 extend outwardly from the elbow 32 to define an increased gap or space between the lower frame portions 36. In this manner, the lower portion of the user's leg may be comfortably positioned between the frame members 26 and 28 without engaging or substantially engaging the frame 14. Thus, the user may comfortably position his leg with the lower portion of the leg brace 10 and engage his foot against the stirrup 18 in a desired location. It should be appreciated that the shape may vary from that depicted in the figures without departing from the scope of the present disclosure.

The first and second frame members 26 and 28 are preferably made from a durable, strong material that may withstand the weight-bearing load of a person up to a certain weight, such as up to 300 pounds. Moreover, the first and second frame members 26 and 28 are preferably made from a sufficiently lightweight material that enables the user to easily move his injured leg with the leg brace 10 when walking. Any suitable material may be used to construct the first and second frame members 26 and 28, such as carbon fiber, or any variation of carbon fiber or a similar material.

Referring to FIGS. 1-4, the first and second frame members 26 and 28 of the frame 14 are adjustably securable to the stirrup 18, wherein the stirrup 18 engages the ground when the person walks and transfers the weight-bearing loads of the user to the frame 14. The stirrup 18 is defined by a substantially U-shaped member having first and second substantially parallel, elongated attachment members 44 and 46 with a ground-engaging member 50 extending therebetween. It should be appreciated that the "ground" may be any surface on which the user is walking.

The ground-engaging member 50 is defined by a tubular member 54 formed from any suitable material in a manner well known in the art. Preferably, the tubular member 54 is hollow to decrease the weight of the tubular member 54 and is made from a durable and strong, yet lightweight material, such as aluminum. The tubular member 54 may be formed integrally with the first and second elongated attachment members 44 and 46 or may instead be formed separately, and thereafter secured to the first and second elongated attachment members 44 and 46 in any suitable manner, such as by welding.

As shown in FIG. 2, the tubular member 54 has a slight curvature along its length to define a slightly convex ground-engaging outer surface 64 and a slightly concave foot-engaging surface 66 extending between the first and second elongated attachment members 44 and 46. Moreover, referring to FIG. 4, the cross-sectional shape of the tubular member 54 is somewhat of an upside down dome shape to define a substantially flat upper cross-sectional portion and a curved, convex bottom cross-sectional portion. As such, the tubular member 54 defines a ground-engaging outer surface 64 that is curved as it extends between the first and second elongated attachment members 44 and 46 and that is curved between the front and rear portions of the tubular member 54.

Figures 3, 4:
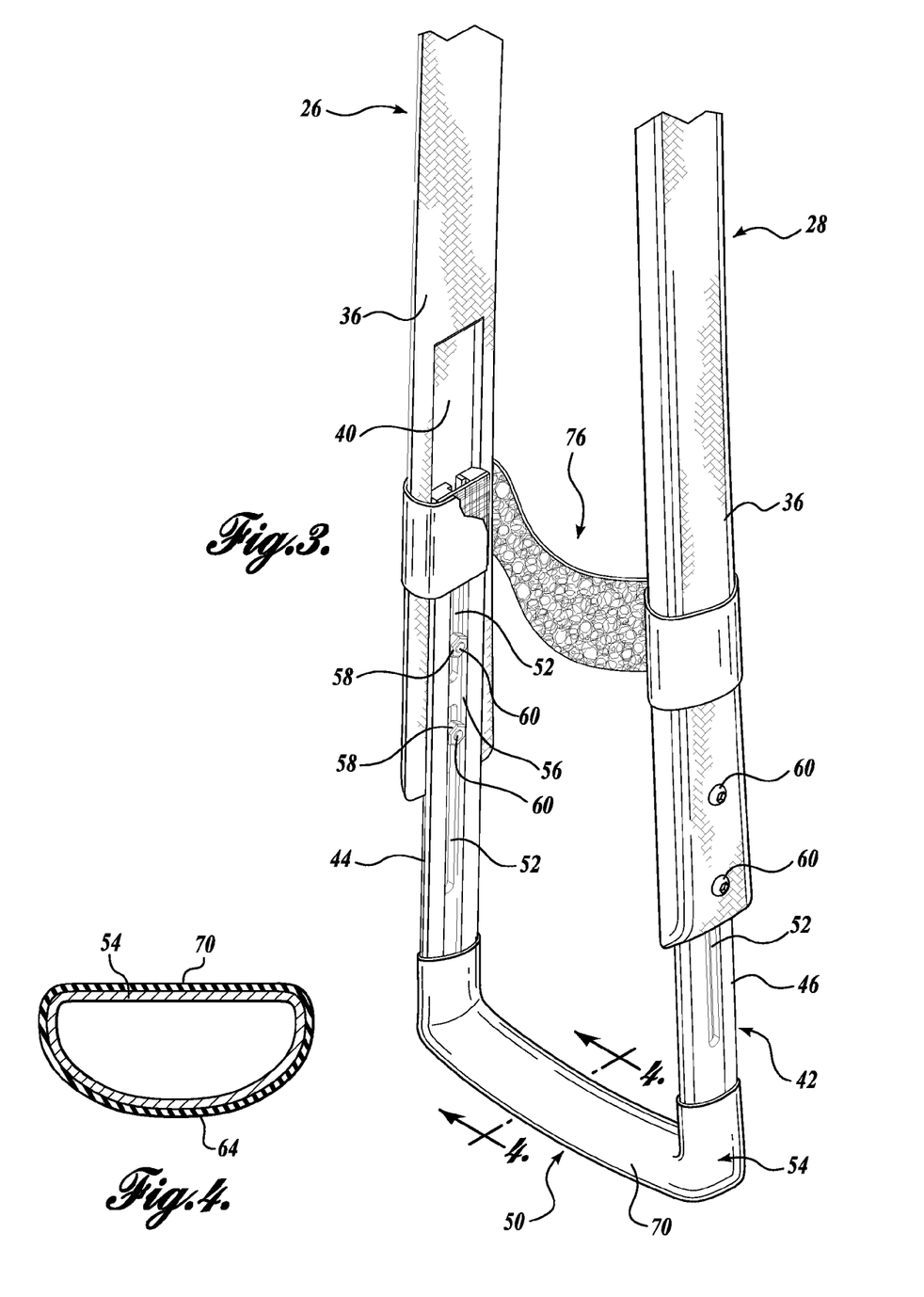
FIG. 3 is an isometric view of a lower portion of the leg brace of FIG. 1.
FIG. 4 is a cross-sectional view of the lower portion of the leg brace of FIG. 3 taken substantially across line 4-4.

With the tubular member 54 having a curvature as described above, the tubular member 54 provides a ground-engaging outer surface 64 that continuously and smoothly engages the ground as the user walks in the leg brace 10. More specifically, the curved ground-engaging outer surface 64 of the tubular member 54 allows the leg brace 10 to rock fore and aft and side to side against the ground as necessary when walking with the leg brace 10. This helps prevent a person from slipping when engaging the ground surface. For instance, if the tubular member 54 was instead substantially square or rectangular in cross-section to define a flat bottom surface, the user would potentially "ice skate" or slip when engaging the ground unless the entire bottom surface of the tubular member was engaged on the ground. The user would also likely slip if the user engaged the ground on an edge of the tubular member.

The curved ground-engaging outer surface 64 of the tubular member 54 also helps propel the user forward as the user is walking, i.e., during the gait cycle. More specifically, as stated above, the curved, ground-engaging outer surface 64 of the tubular member 54 allows the leg brace 10 to rock fore and aft against the ground. As such, the user can rock forward on the ground-engaging outer surface 64 of the tubular member 54 as the user engages the tubular member 54 against the ground and moves forward to contact the other, non-injured foot with the ground. Thus, the curved, ground-engaging outer surface 64 of the tubular member 54 provides a safe, ground-engaging surface that aids the user during the gait cycle.

Referring to FIGS. 3 and 4, the tubular member 54 and at least a portion of the first and second attachment members 44 and 46 are preferably covered with a suitable, non-slip cover 70 that helps prevent the user from slipping when engaging the ground. The non-slip cover 70 may be formed from any suitable non-slip material, such as rubber, and it may be secured on the tubular member 54 in any suitable manner. For instance, the non-slip cover 70 may initially be of a cylindrical, tubular form such that it may be slidably positioned over the tubular member 54 and at least a portion of the first and second attachment members 44 and 46. The cover 70 may be thereafter heated to conform to the shape of and mold onto the tubular member 54 and at least a portion of the first and second attachment members 44 and 46. It should be appreciated that the non-slip cover 70 may instead be applied to the tubular member 54 and at least a portion of the first and second attachment members 44 and 46 in any other suitable manner. Moreover, the non-slip cover 70 may instead be an integral portion of or otherwise formed on the stirrup 18.

Referring to FIG. 3, the stirrup 18 is adjustably securable to the first and second frame members 26 and 28 of the frame 14 to customize the size of the leg brace 10 for different individuals. More specifically, the position of the stirrup 18 is adjusted on the frame 14 to increase or decrease the overall length of the leg brace 10 such that the stirrup 18 is comfortably engageable with the ground when the person is walking without the person's foot engaging the stirrup 18 and bearing substantial weight.

The stirrup 18 is adjustably securable to the frame 14 by adjustably securing the first and second attachment members 44 and 46 to the lower frame portions 36 of the first and second frame members 26 and 28. Each of the first and second attachment members 44 and 46 are slidably receivable at least partially within cavities 40 (only one cavity 40 shown for clarity) formed on the interior lower frame portion 36 of each of the first and second frame members 26 and 28. The cavities 40 extend along at least a portion of the lower frame portion 36 and intersect the lower edge of the frame members 26 and 28. The first and second attachment members 44 and 46 may be slidably positioned within the cavities 40 to appropriately position the stirrup 18 on the frame 14 before securing the stirrup 18 to the frame 14.

The first and second attachment members 44 and 46 are adjustably securable to the first and second frame members 26 and 28 of the frame 14 in any suitable manner well known in the art. Preferably, each of the first and second attachment members 44 and 46 include at least one slot 52 extending along at least a portion of its length that is configured to adjustably receive a fastener therein. In the embodiment illustrated, the first and second attachment members 44 and 46 each include two slots 52, wherein each slot adjustably receives a fastener therein to secure the frame 14 to the stirrup 18.

The slots 52 are formed within a longitudinal recess 56 defined along the interior surface of each attachment member 44 and 46. The longitudinal recess 56 is of a certain depth and width such that a nut 58 may be slidably received therein and prevented from rotating within the recess. As such, a fastener 60 may be threaded into each nut 58 while the position of the nut 58 is maintained. Thus, to secure the frame 14 to the stirrup 18, fasteners 60 are passed through an opening in the lower frame portion 36 of each of the first and second frame members 26 and 28 and threaded into a nut 58 positioned within the longitudinal recess 56. Any suitable fastener 60 may be used, such as a hex socket head cap screw that includes a hex socket in the head to accept a hex wrench to tighten the screw into the nut 58. However, it should be appreciated that any other suitable fastener or screw and nut assembly may instead be used.

Referring to FIGS. 1-3, a shin strap 76 is adjustably secured to the leg brace 10 to maintain the position of the lower portion of the user's leg within the leg brace 10. Preferably, the shin strap 76 extends between the first and second attachment members 44 and 46 of the stirrup 18. The shin strap 76 is made from a flexible and sturdy material or fabric, such as nylon, such that the shin of the user may comfortably abut against the strap 76 and apply a significant amount of pressure against the strap 76 when in use.

The shin strap 76 may be adjustably connected to the first and second attachment members 44 and 46 with a suitable attachment assembly, such as a hook and loop type fastener assembly. For instance, in the embodiment shown, a piece of hook material 80 is adhered to or otherwise secured to the upper end of each of the first and second attachment members 44 and 46. The shin strap 76 is defined by a piece of loop material 84 that extends between the first and second attachment members 44 and 46 and is releasably secured to the hook material 80. Preferably, the shin strap 76 extends around the first and second frame members 26 and 28 of the frame 14 and is thereafter releasably secured to the hook material 80. Moreover, the shin strap 76 is positioned such that it extends across the rear of the first and second frame members 26 and 28 with the loop portion of the material 84 facing away from the user's leg. As such, the material 84 may wrap around the first and second frame members 26 and 28 and be releasably and adjustably secured to the hook material 80.

The shin strap 76 is secured to the first and second attachment members 44 and 46 such that is has a predetermined amount of sag in the strap to allow a user's shin to comfortably rest against and engage the strap 76 during use. The amount of sag can be changed by adjusting the attachment position of the loop material 84 on the hook material 80 to increase or decrease the length of the strap 76 extending between the first and second attachment members 44 and 46. The loop material 84 is of a sufficient length such that the sag may be sufficiently decreased or increased to accommodate most users.

The shin strap 76 is also at a predetermined vertical position relative to the frame 14 such that the user's shin may engage the strap 76 to prevent the user's leg from swinging forward out of the brace 10 and potentially hitting the ground during use. Preferably, the shin strap 76 is secured to the first and second attachment members 44 and 46 at an appropriate vertical location such that when the stirrup 18 is appropriately positioned on the frame 14, the shin strap 76 is engageable with the user's shin in a suitable location.

The shin strap may instead be adjustably coupled to the first and second attachment members 44 and 46 or any other portion of the leg brace 10 in any other suitable manner. Thus, it should be appreciated that the foregoing description should not be seen as limiting the scope of the present disclosure.

Referring to FIGS. 5 and 6, the attachment assembly 22 for adjustably securing the leg brace 10 to a user's leg will be hereinafter described in detail. The attachment assembly 22 includes first and second thigh-engaging portions 100 and 104 that are correspondingly-shaped to engage and wrap around the thigh of the user to tightly secure the leg brace 10 to the user. The first and second thigh-engaging portions 100 and 104 are each comprised of an interior padded portion 108 and an exterior semi-rigid backing portion 112. The exterior semi-rigid backing portion 112 is of substantially the same shape as the interior padded portion 108 yet preferably somewhat smaller in size such that the perimeter of the exterior semi-rigid backing portion 112 is offset inwardly from the perimeter of the interior padded portion 108 to define a soft, flexible edge of the thigh-engaging portions 100 and 104. However, it should be appreciated that the exterior semi-rigid backing portion 112 may instead be substantially the same size as the interior padded portion 108.

The interior padded portion 108 is preferably made from a durable, soft, lightweight, and preferably somewhat stretchable material that comfortably wraps around the user's leg. For instance, the interior padded portion 108 may be made from neoprene or another similar material commonly used for athletic braces. The exterior surface of the interior padded portion 108 is preferably covered with a layer of loop material 110 that is detachably adherable to pieces of hook material (not shown) secured to the interior surface of the exterior semi-rigid backing portion 112. In this manner, the interior padded portion 108 may be removed for cleaning or adjusted in its position on the exterior semi-rigid backing portion 112 for use with different persons.

The interior padded portion 108 of each thigh-engaging portion 100 and 104 is removably secured to the upper frame portions 34 of each of the first and second frame members 26 and 28 through the exterior semi-rigid backing portion 112. The exterior semi-rigid backing portion 112 is secured to the first and second frame members 26 and 28 in any suitable manner, such as with a plurality of fasteners. The exterior semi-rigid backing portion 112 is preferably made from a semi-rigid plastic material that is bendable to conform to the shape of the user's leg, yet sufficiently durable to remain secured to the upper frame portions 34 of each of the first and second frame members 26 and 28 when the leg brace 10 is being used. Moreover, the exterior semi-rigid backing portion 112 is defined by a substantially large surface area of material to resist tearing under shear loads.

As mentioned above, the first and second thigh-engaging portions 100 and 104 are correspondingly shaped to engage and wrap around the thigh of the user to tightly secure the leg brace 10 to the user. Although the first and second thigh-engaging portions 100 and 104 may be any suitable shape, the first thigh-engaging portion 100 preferably includes front upper and lower flaps 116 and 120 extending forwardly of the first frame member 26. A front middle flap 124 formed on the second thigh-engaging portion 104 extends between the front upper and lower flaps 116 and 120 when the front upper, lower, and middle flaps 116, 120, and 124 are wrapped around a front portion of the user's thigh.

The first and second thigh-engaging portions 100 and 104 similarly fit together around a back portion of the user's thigh. More specifically, the second thigh-engaging portion 104 includes rear upper and lower flaps 122 and 126 extending rearwardly of the first frame member 26, and the first thigh-engaging portion 100 includes a rear middle flap 118 that extends between the rear upper and lower flaps 122 and 126 when the rear upper, lower, and middle flaps 122, 126, and 118 are wrapped around a back portion of the user's thigh.

The attachment assembly 22 further includes first, second, and third tightening or closure assemblies 138, 142, and 146 extending around and joining the first and second thigh-engaging portions 100 and 104 to tightly secure the leg brace 10 to a user's leg. The first, second, and third closure assemblies 138, 142, and 146 are substantially identical in design, and therefore, for the sake of brevity, only the first closure assembly 138 will be described in detail.

The first closure assembly 138 includes a strap 152 extending around the exterior of an upper portion of the first and second thigh-engaging portions 100 and 104 such that the strap 152 is engageable with the front and rear upper flaps 116 and 122. The strap 152 includes first and second sides 154 and 156, wherein the first side 154 is engageable with the exterior of the first and second thigh-engaging portions 100 and 104 when the strap 152 is appropriately positioned around the first and second thigh-engaging portions 100 and 104. The second side 156 is defined by loop material secured thereon or integrally formed as a portion of the strap 152 that is used for securing the strap 152 in its position, as will be described below.

The strap 152 further includes a shortened end 158 and an elongated end 160. The shortened end 158 is defined by a portion of the strap 152 that passes between the second thigh-engaging portion 104 and the second frame member 28 and thereafter loops through a ring 164. After looping through the ring 164, the strap 152 is secured onto itself or a portion of the second thigh-engaging member 104 in any suitable manner, such as by sewing, to position the ring 164 forwardly of the second frame member 28. The ring 164 preferably defines an opening that is somewhat rectangular in shape and sized to receive the elongated end 160 of the strap 152 therethrough.

The strap 152 extends from the shortened end 158 around the back portion of the first and second thigh-engaging portions 100 and 104 and passes between the first thigh-engaging portion 100 and the first frame member 26 to define the elongated end 160 of the strap 152. The elongated end 160 extends forwardly of the first frame member 26 and is of a predetermined length such that it may extend across the front portions of the first and second thigh-engaging portions 100 and 104, pass through the ring 164, and fold back over onto itself. A piece of hook material 174 is secured onto the second side 156 of the strap 152 near the end of the elongated end 160 that is releasably engageable with the loop material on the second side 156 of the strap 152 when the strap is folded over onto itself. As such, the strap 152 may be pulled through the ring 164 a predetermined amount, depending on the circumference of the user's thigh, and thereafter folded over onto itself and releasably secured in its position. As such, the first closure assembly 138 is adjustable and adapted for use with a variety of users.

The strap 152 may be further adjustably securable around the user's thigh through at least one piece of hook material 168 secured on the first side 154 of the strap 152 that is releasably securable to at least one piece of loop material 170 secured onto the semi-rigid backing portion 112. Preferably, the at least one piece of loop material 170 is secured to the area of the semi-rigid backing portion 112 covering the front upper flap 116. The hook material 168 is secured on the first side of the strap 154 such that it is engageable with the loop material 170 when pulled forwardly of the first frame member 26.

More specifically, the elongated end 160 of the strap 152 may be pulled forwardly of the first frame member 26 to tighten the strap 152 against the back portions of the first and second thigh-engaging portions 100 and 104 and against the back of the user's thigh. The strap 152 may then be first secured against the first flap 116 by engaging the hook material 168 with the loop material 170. In this manner, the strap 152 may be held in a substantially taut position against the back of the first and second thigh-engaging portions 100 and 104 when the elongated end 160 of the strap 152 is passed over the front portions of the first and second thigh-engaging portions 100 and 104 and through the ring 164. The user can then further tighten the strap 152 around his or her leg by pulling the elongated end 160 a desired amount through the ring 164 and thereafter securing the hook portion 174 onto the second side 156 of the strap 152.

The second and third closure assemblies 142 and 146 of the attachment assembly 22 are used to tighten the middle and lower portions of the first and second thigh-engaging portions 100 and 104 around the user's thigh in substantially the same manner as described above with respect to the first closure assembly 138. More specifically, the second closure assembly 142 wraps the middle front and rear flaps 124 and 118 around the user's thigh, and the third closure assembly wraps the lower front and rear flaps 120 and 126 around the user's thigh (see FIG. 1). Moreover, as described above, the upper and lower front and rear flaps of each thigh-engaging member oppose and mate with the front and rear middle flaps of the other thigh-engaging member. As such, the straps of the first and third closure assemblies 138 and 146 are pulled in a direction opposite the strap of the second closure assembly 142 to wrap the flaps of the first and second thigh-engaging portions 100 and 104 around the thigh of the user. These opposing pulling forces created by the closure assemblies creates a substantially symmetrical distribution of strap loads to help prevent the attachment assembly 22 from "twisting" in one direction when secured to the user's thigh.

As discussed briefly above, the upper frame portion 34 of each of the first and second frame members 26 and 28 extends at least somewhat outwardly from the elbow 32 such that the attachment assembly 22 has an overall generally frusto-conical shape, similar to that of the user's thigh. More specifically, the first and second thigh-engaging portions 100 and 104, when secured around the user's thigh, define an overall cross-sectional shape that is smaller in diameter near the bottom and larger in diameter near the top. As such, the attachment assembly 22 generally conforms to the shape of the user's thigh and helps prevent the user's thigh from slipping downwardly through the attachment assembly 22 when the weight-bearing load of the user is transferred to the thigh during use. The user's thigh would likely slip downwardly through the attachment assembly 22 if, for instance, the overall shape of the attachment assembly 22 was generally cylindrical to define a substantially constant cross-sectional shape.

The tapered bottom of the attachment assembly 22 prevents the user's thigh from slipping downwardly when the leg brace 10 bears the weight of the user. If a non-tapered generally cylindrical shape was instead used, the user would necessarily over-tighten the straps of the closure assembly to help prevent slippage. However, over-tightening the straps can reduce circulation of blood within the user's leg and can cause discomfort to the user. Moreover, it has been found that even when over-tightening the straps on an attachment assembly having a constant cross-sectional shape, the user's thigh slips during use. Thus, the generally frusto-conical shape of the attachment assembly 22 helps prevent slippage of the user's thigh within the attachment assembly 22 and increases the comfort during the use of the leg brace 10.

Referring to FIG. 1, the manner in which the leg brace 10 is used by an injured patient, or user, will now be described in detail. If the leg brace 10 is being used for the first time by the specific user, the length of the frame 14 is first adjusted such that the ground-engaging member 50 of the stirrup 18 will comfortably engage the ground when the attachment assembly 22 is secured around a portion of the patient's thigh. However, the length of the frame 14 is not too short such that the foot of the user engages the stirrup 18 and bears substantial weight during use. It should be appreciated that the user's foot may be suspended above the stirrup 18, or it may instead be resting on the stirrup 18 during use.

To adjust the length of the frame 14, the position of the stirrup 18 is adjusted relative to the first and second frame members 26 and 28 by sliding the first and second elongated attachment members 44 and 46 within the cavities 40 of the first and second frame members 26 and 28. Once the stirrup 18 is in a desired location, the fasteners 60 are used to secure the first and second elongated attachment members 44 and 46 to the first and second frame members 26 and 28 as described in detail above with respect to FIG. 3. If necessary, the shin strap 64 is adjusted to increase or decrease the sag in the strap to accommodate the circumference of the user's lower leg such that the user's foot may either be suspended above the ground-engaging member 50 of the stirrup 18 or comfortably rest thereon. After adjusting the length of the frame 14, the user secures the leg brace 10 to his or her thigh with the attachment assembly 22.

Once the leg brace 10 is securely fastened to the user's leg, the user may walk with the leg brace 10 acting as a substantial replacement or prosthetic for the injured leg. More specifically, as the user steps forward onto the injured leg, the ground-engaging member 50 of the stirrup 18 engages the ground and transfers the weight-bearing load of the user to the frame 14, which in turn transfers the load to the user's thigh. As such, the user may walk on the injured leg without bearing any weight on the injured portion and without restricting the user's arms. Having the ability to walk on the injured leg without bearing any weight on the injured portion gives the user increased mobility while allowing the injured portion to heal. Moreover, the upper portion of the injured leg and the hip area above the injured leg are still used to walk with the leg brace 10, thereby minimizing atrophy of the muscles in the injured leg.

Figure 7:
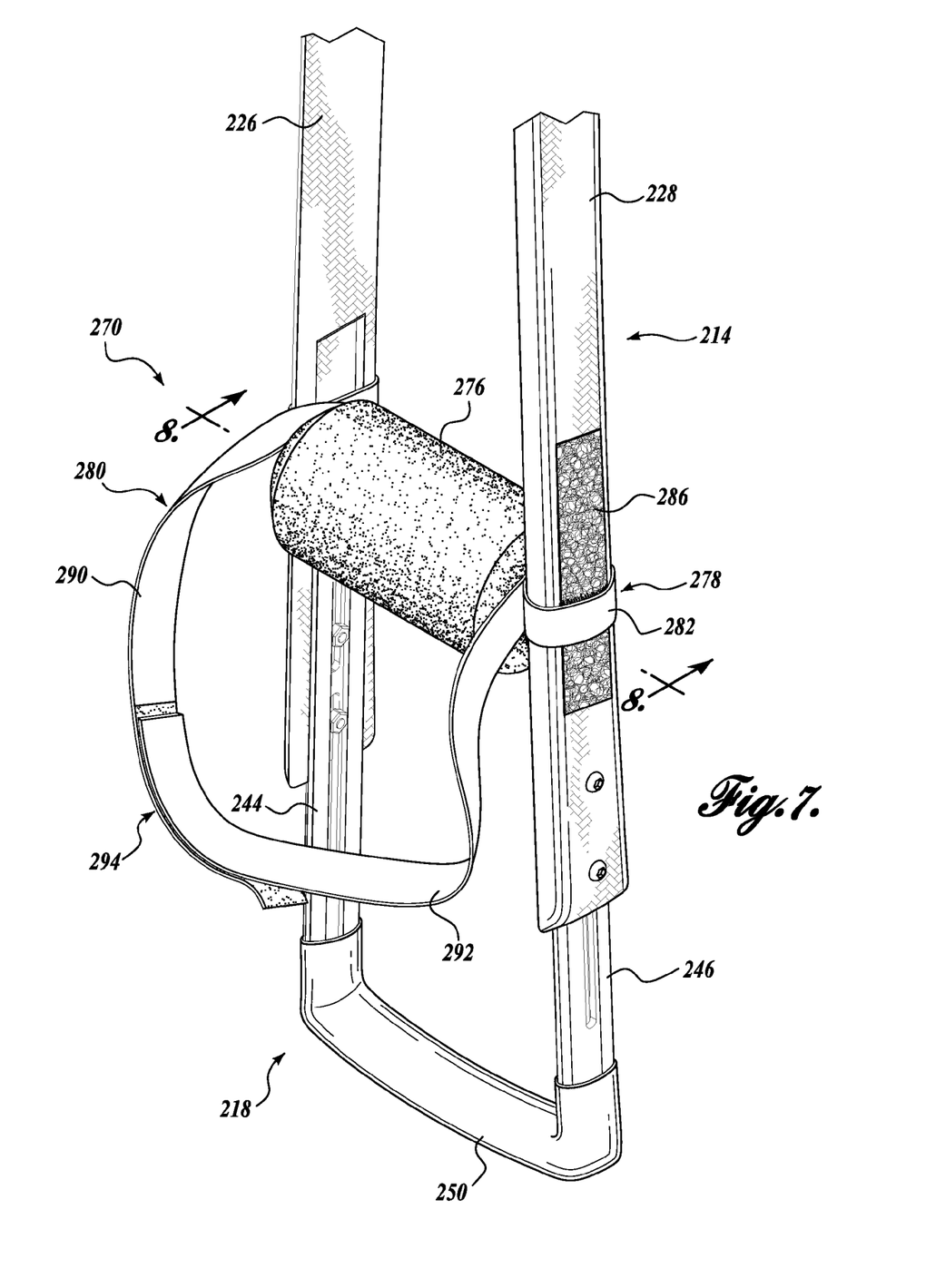
FIG. 7 is an isometric view of a lower portion of the leg brace of FIG. 1.
Figure 8:
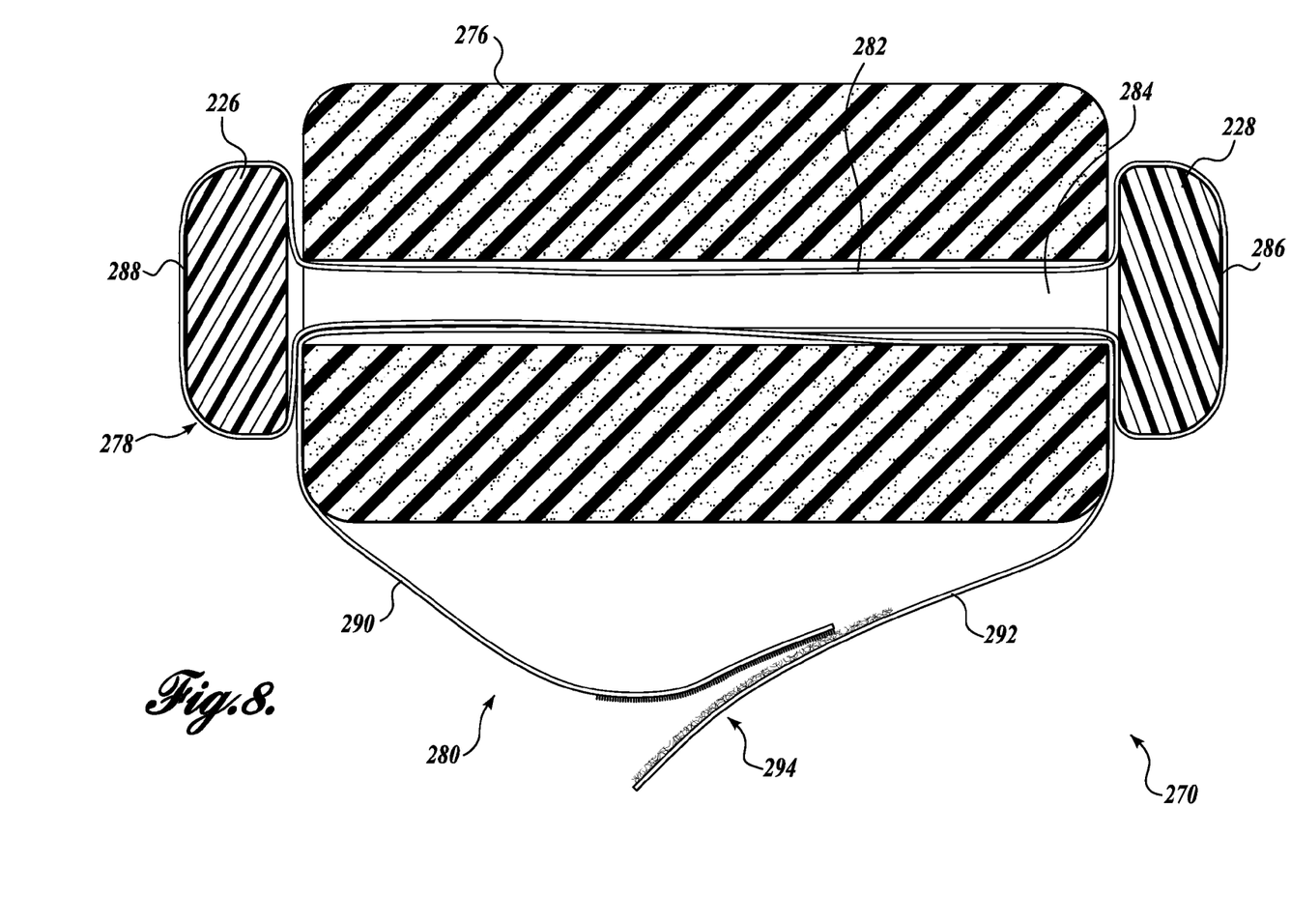
FIG. 8 is a cross-sectional view of the lower portion of the leg brace of FIG. 7 taken substantially across line 8-8.

Referring to FIGS. 7 and 8, an alternate embodiment of a leg brace (shown only partially) having a lower leg attachment assembly 270 will now be described in detail. The lower leg attachment assembly 270 is configured for use with a leg brace having a stirrup 218 substantially identical to stirrup 18 described above. Briefly described, the stirrup 218 is defined by a substantially U-shaped member having first and second substantially parallel, elongated attachment members 244 and 246 with a ground-engaging member 250 extending therebetween.

The first and second attachment members 244 and 246 are adjustably secured to first and second frame members 226 and 228 of the frame 214 of the leg brace to customize the size of the leg brace for different individuals. More specifically, the position of the stirrup 218 is adjusted on the first and second frame members 226 and 228 to increase or decrease the overall length of the leg brace such that the stirrup 218 is comfortably engageable with the ground when the person is walking without the person's foot engaging the stirrup 218 and bearing substantial weight. The stirrup 218 engages the ground when the person walks and transfers the weight-bearing loads of the user to the frame 214 of the leg brace.

The lower leg attachment assembly 270 is adjustably secured to the frame 214 and/or the stirrup 218 to engage a lower portion of the user's leg. The lower leg attachment assembly 270 includes a shin pad 276 and a calf strap 280 that are positioned to engage the lower portion of the user's leg to help stabilize and position the leg within the brace during use.

The shin pad 276 extends between the first and second frame members 226 and 228 of the frame 214 (and/or the first and second attachment members 244 and 246 of the stirrup 218). The shin pad 276 may be any suitable design for engaging the shin of a user's leg. In the depicted embodiment, the shin pad 276 is embodied as a cylindrical member made from a pliable material, such as foam. The curved exterior surface of the shin pad 276 is positioned to engage the user's shin, with the substantially transverse ends abutting against or positioned near the interior surface of the first and second frame members 226 and 228 of the frame 214. It should be appreciated that the shin pad 276 may instead be contoured similar to that of the shin strap 76 described above or may instead be any other shape and configuration to comfortably engage the shin of a user during use.

As discussed above with reference to the leg brace 10, the size of the leg brace is customizable to accommodate individuals of varying heights, weights, etc. Along the same lines, the shin pad 276 is releasably and adjustably secured to the frame 214 in one of various vertical and horizontal positions (relative to substantially vertical first and second frame members 226 and 228 of the frame 214) to appropriately engage a portion of the user's shin and to position the user's leg and foot in a desired position relative to the leg brace. For instance, if the user has a leg amputated below the knee, the vertical position of the shin pad 276 would in most instances need to be raised to a higher location such that the shin pad 276 was engageable with the leg.

As another example, the horizontal and/or vertical position of the shin pad 276 can dictate how far the user's foot protrudes forwardly through the stirrup 218. More specifically, if the shin pad 276 is positioned too low and/or too far forward within the leg brace, the front of a user's foot could unintentionally engage the ground surface during use. Thus, the vertical and/or horizontal position of the shin pad 276 could be adjusted to appropriately engage and position the user's leg and foot within the leg brace.

The shin pad 276 may be adjustably and releasably connected to the first and second frame members 226 and 228 of the frame 214 with a suitable attachment assembly, such as a strap assembly 278. The strap assembly 278 is defined by an elongated strap 282 that is secured to both the shin pad 276 and the first and second frame members 226 and 228 of the frame 214. Although the strap 282 may be secured to the shin pad 276 in any suitable manner, in the depicted embodiment, the strap 282 passes through an elongated, center axial opening 284 in the shin pad 276.

More specifically, the strap 282 may pass through the elongated opening 284, around each of the first and second frame members 226 and 228, back through the elongated opening 284, and out from the elongated opening 284 to terminate in first and second strap ends 290 and 292. To help releasably secure the strap 282 (and, therefore, the shin pad 276) to the frame 214, first and second pieces of loop material 286 and 288 may be secured to the exterior surfaces of the first and second frame members 226 and 228, respectively. The strap 282 may correspondingly include first and second pieces of hook material (not shown) along at least a portion of the interior surface of the strap 282 that are engageable with the first and second pieces of loop material 286 and 288 to releasably secure the strap 282 to the frame 214. The first and second pieces of loop material 286 and 288 may extend along a portion of the length of the exterior surfaces of the first and second frame members 226 and 228 such that the strap 282 (and, therefore, the shin pad 276) may be releasably secured to the lower portion of the frame 214 at any desired vertical location on the frame 214.

The strap assembly 278 may also be used to adjust the horizontal position of the shin pad 276 relative to the first and second frame members 226 and 228 of the frame 214. Referring specifically to FIG. 8, the strap 282 may be loosened, pulled, or otherwise adjusted in its position within the central opening 284 of the shin pad 276 to reposition the shin pad 276 horizontally within the frame 214. For example, if the shin pad 276 is pushed away from the calf strap 280 (to move the shin pad 276 forwardly relative to the frame 214), certain portions of the strap 282 will either be loosened or tightened to accommodate the new position. In that regard, the first and second strap ends 290 and 292 may be pulled to tighten the strap assembly 278 or take up any slack in the strap 282.

Once the shin pad 276 is appropriately positioned relative to the frame 214 and stirrup 218, the calf strap 280 may be used to help secure the user's leg against the shin pad 276. The first and second strap ends 290 and 292 of the strap 282 extend from the shin pad 276 and are connectable together with an adjustable strap attachment assembly 294 to define the calf strap 280. In the depicted embodiment, the adjustable strap attachment assembly 294 is a hook-and-loop-type fastener. A pad or other cushioning device (not shown) may be secured to an interior portion of the calf strap 280 to engage the user's leg to create a more comfortable experience for the user.

With the use of the hook-and-loop-type fastener or any other suitable adjustable strap attachment assembly, the overall length of the calf strap 280 may be adjusted to accommodate calves or leg portions of varying circumferences. It should be appreciated that any suitable adjustable strap attachment assembly may be used, such as a clasp, buckle, etc. Moreover, it should be appreciated that the calf strap 280 may instead be an independent strap assembly separate from the strap assembly 278 used to secure the shin pad 276 to the frame 214. Thus, the foregoing description should not be construed as limiting the scope of the claimed subject matter.

As can be appreciated from the foregoing, the lower leg attachment assembly 270 is used to releasably secure and position the lower portion of a user's leg relative to the frame 214. With the user's leg appropriately positioned and secured to the lower portion of the frame 214, the user will likely have an increased sensation that the leg brace is an extension of his or her leg, similar to a prosthetic device.

While the preferred embodiment of the leg brace has been illustrated and described, it will be appreciated that various changes can be made therein without departing from the spirit and scope of the present disclosure.

The embodiments of the invention in which an exclusive property or privilege is claimed is defined as follows:

1. A leg brace configured for use on a ground surface with a user having a body weight and first and second legs, the leg brace adapted to be secured to a user's first leg having upper and lower leg portions, a knee between the upper and lower leg portions, and a bottom end defined by the lower leg portion opposite the upper leg portion, the leg brace configured to secure the user's knee in a fixed, bent position such that an overall length of the leg brace is substantially equal in length to the second leg when the user is walking, the leg brace comprising:

(a) a frame comprising at least a first frame member and a second frame member, each of the first and second frame members having an upper frame portion and a lower frame portion, wherein each upper frame portion extends rearwardly from a vertical axis defined by the corresponding lower frame portion such that each of the first and second frame members have a slight permanent bend that defines an elbow between the upper frame portion and the lower frame portion of the first and second frame members;

(b) a stirrup having first and second frame attachment members and a ground-engaging portion extending between the first and second frame attachment members, wherein the first and second frame attachment members are adjustably and rigidly secured to the first and second frame members to selectively adjust the overall length of the leg brace such that the bottom end of the first leg is adapted to be positioned above the ground-engaging portion when the leg brace is secured on the first leg and such that the overall length of the leg brace is substantially equal in length to the second leg when the user is walking;

(c) a first attachment assembly coupled to the upper frame portion of each of the first and second frame members, the first attachment assembly configured to removably secure the frame to the upper leg portion such that the upper leg portion is adapted to be positioned between the upper frame portions of the first and second frame members, and the leg brace is configured to bear the body weight of the user through the upper leg portion such that the lower leg portion, the knee, and the bottom end of the lower leg portion do not bear the body weight and the bottom end of the lower leg portion may avoid contact with both the stirrup and the ground surface when the leg brace is in use, the lower leg portion is adapted to be positioned between the lower frame portions of the first and second frame members, and the knee is adapted to be positioned between the elbows of the first and second frame members; and (d) a second attachment assembly adjustably coupled to the lower frame portions of the first and second frame members, the second attachment assembly configured to removably secure the lower leg portion to the lower frame portions of the first and second frame members such that the user's knee is adapted to be maintained in a fixed, bent position for walking.

2. The leg brace of claim 1, wherein the first attachment assembly includes at least one attachment member defined by a semi-rigid material that is configurable into a substantially frusto-conical shape for substantially conforming to the shape of the user's leg.

3. The leg brace of claim 2, wherein the semi-rigid material of the at least one attachment member is configured to transfer a load from the upper portion of the user's leg to the frame.

4. The leg brace of claim 2, wherein the first attachment assembly has at least first and second enclosure straps, each of the first and second enclosure straps configured to secure together first and second portions of the at least one attachment member, the first and second enclosure straps arranged in opposing directions.

5. The leg brace of claim 1, wherein the ground-engaging portion of the stirrup is arcuate in shape.

6. The leg brace of claim 5, wherein the ground-engaging portion is substantially dome-shaped in cross section.

7. The leg brace of claim 5, wherein the ground-engaging portion defines a non-slip exterior surface.

8. The leg brace of claim 1, wherein the second attachment assembly includes a padded portion engageable with the lower leg portion of the user's leg.

9. A method for using a leg brace on a ground surface with a user having a body weight and first and second legs, the first leg having upper and lower leg portions, a knee between the upper and lower leg portions, and a bottom end defined by the lower leg portion opposite the upper leg portion, the leg brace configured to secure the user's knee in a fixed, bent position such that an overall length of the leg brace is substantially equal in length to the second leg when the user is walking, the method comprising:

(a) providing a leg brace, comprising:
  (i) a frame having at least a first frame member and a second frame member, each of the first and second frame members having an upper frame portion and a lower frame portion, wherein each upper frame portion extends rearwardly from a vertical axis defined by the corresponding lower frame portion such that each of the first and second frame members have a slight permanent bend that defines an elbow between the upper frame portion and the lower frame portion of the first and second frame members;
  (ii) a stirrup having first and second frame attachment members and a ground-engaging portion extending between the first and second frame attachment members, wherein the first and second frame attachment members are adjustably and rigidly secured to the first and second frame members to selectively adjust the overall length of the leg brace such that the bottom end of the first leg is adapted to be positioned above the ground-engaging portion when the leg brace is secured on the first leg and such that the overall length of the leg brace is substantially equal in length to the second leg when the user is walking;
  (iii) a first attachment assembly coupled to the upper frame portion of each of the first and second frame members; and
  (iv) a second attachment assembly adjustably coupled to the lower frame portion of each of the first and second frame members;

(b) removably securing the first attachment assembly to the upper leg portion such that the upper leg portion is adapted to be positioned between the upper frame portions of the first and second frame members, and the leg brace is configured to bear the body weight of the user through the upper leg portion such that the lower leg portion, the knee, and the bottom end of the lower leg portion do not bear the body weight and the bottom end of the lower leg portion may avoid contact with both the stirrup and the ground surface when the leg brace is in use, the lower leg portion is adapted to be positionable between the lower frame portions of the first and second frame members, and the knee is adapted to be positioned between the elbows of the first and second frame members; and (c) removably securing the second attachment assembly to the lower leg portion such that the user's knee is adapted to be in a fixed, bent position for walking.

10. The method of claim 9, wherein the first attachment assembly includes at least one attachment member defined by a semi-rigid material that is configurable into a substantially frusto-conical shape for substantially conforming to the shape of the user's leg.

11. The method of claim 10, wherein the semi-rigid material of the at least one attachment member is configured to transfer a load from the upper portion of the user's leg to the frame.

12. The method of claim 10, wherein the first attachment assembly has at least first and second enclosure straps, each of the first and second enclosure straps configured to secure together first and second portions of the at least one attachment member, the first and second enclosure straps arranged in opposing directions.

13. The method of claim 9, wherein the ground-engaging portion of the stirrup is arcuate in shape.

14. The method of claim 13, wherein the ground-engaging portion is substantially dome-shaped in cross section.

15. The method of claim 13, wherein the ground-engaging portion defines a non-slip exterior surface.

16. The method of claim 9, wherein the second attachment assembly includes a padded portion engageable with the lower leg portion of the user's leg.

* * * * *